United States Patent [19]

Schroeder

[11] Patent Number: 4,813,936

[45] Date of Patent: Mar. 21, 1989

[54] RETRACTING HYPODERMIC NEEDLE

[75] Inventor: Miles D. Schroeder, Greenfield, Ind.

[73] Assignee: Geralyn M. Schroeder, Greenfield, Ind.

[21] Appl. No.: 145,916

[22] Filed: Jan. 20, 1988

[51] Int. Cl.⁴ .............................................. A61M 5/32
[52] U.S. Cl. .................................... 604/195; 604/263
[58] Field of Search ............... 604/198, 197, 196, 195, 604/194, 218, 228, 232, 263, 110

[56] References Cited

U.S. PATENT DOCUMENTS 2,722,215 11/1955 Dahlgren ...................... 604/228 X
2,880,725 4/1959 Kendall ............................. 604/196
2,888,924 6/1959 Dunmire ............................ 604/196

*Primary Examiner*—John D. Yasko
*Attorney, Agent, or Firm*—Woodard, Emhardt, Naughton Moriarty & McNett

[57] ABSTRACT

A disposable needle assembly for a hypodermic syringe. A hypodermic needle is slidably mounted to a syringe main body having removably inserted therein a glass anesthetic carpule. The inwardly positioned end of the needle extends piercingly into the carpule. A plunger slidably mounted to the syringe main body has an inwardly positioned end secured to a rubber stopper slidably mounted within the carpule. Inward movement of the plunger forces the stopper toward the needle inner end injecting the material within the carpule outwardly and eventually affixing the needle inner end to the stopper. Retraction of the plunger pulls the needle completely into the carpule for subsequent destruction therewith.

19 Claims, 2 Drawing Sheets

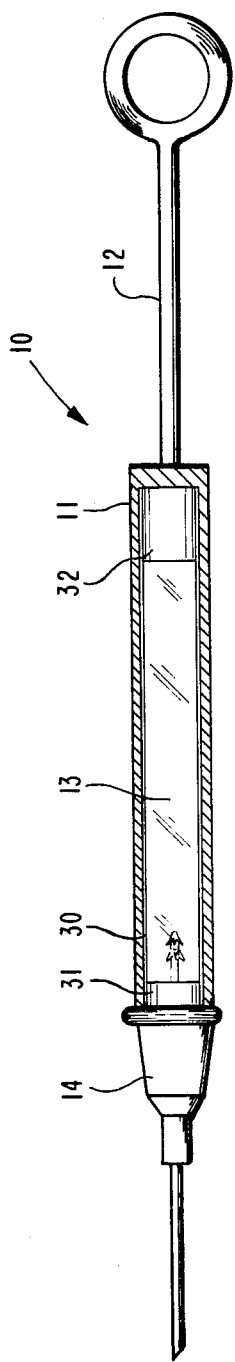
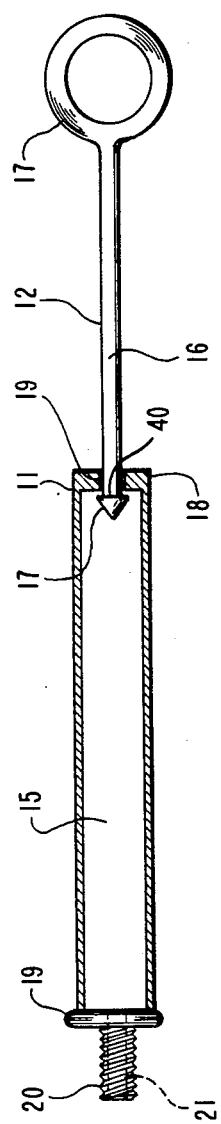
Fig. 1
Fig. 2

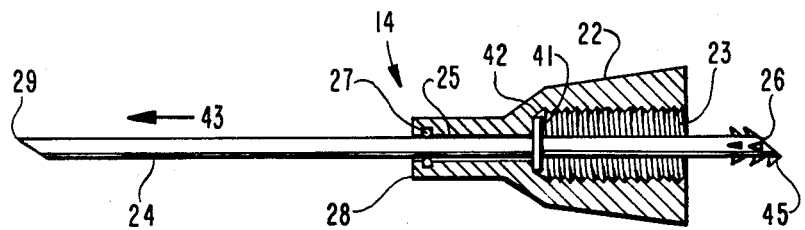
Fig. 3
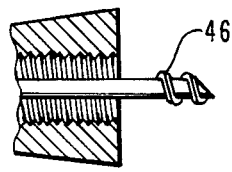
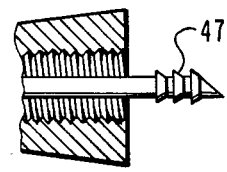
Fig. 4  Fig. 5
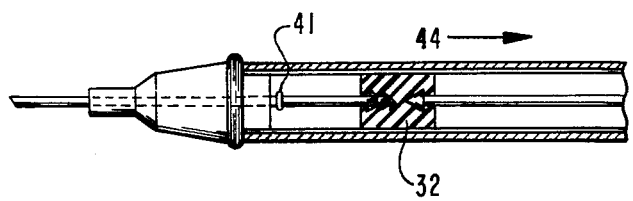
Fig. 6

RETRACTING HYPODERMIC NEEDLE

FIELD OF THE INVENTION

This invention is in the field of medical implements and particularly hypodermic syringes.

BACKGROUND OF THE INVENTION

A conventional hypodermic syringe includes a removable needle which is discarded along with the emptied glass anesthetic carpule after each use of the syringe. Once the needle is used, the needle poses a danger not only to the doctor or nurse handling the syringe, but anyone coming into contact with the needle. A variety of different types of devices have been provided for disposing of the needle and carpule such as various grinding machines for destroying and holding the discarded needle and carpule. Likewise, the various shields or containers have been provided into which the needle may be inserted prior to discarding. All of the devices, covers and shields heretofore provided require further handling of the needle from the point of patient use to the final destruction or storage. I have therefore devised a needle assembly which is operable together with the syringe plunger to withdraw the needle into the carpule upon completion of use of the syringe thereby completely isolating the needle immediately after the patient is injected and allowing the carpule to subsequently be discarded with the needle therein.

SUMMARY OF THE INVENTION

One embodiment of the present invention is a needle assembly for mounting to a hypodermic syringe comprising a hollow needle with a pointed outer end and an inner end, and, mounting means including a main body removably mountable on the syringe and further including a passage in the main body through which the needle extends and is slidable, the needle and the main body including cooperating stop means limiting outward movement of the needle relative to the main body but not limiting inward movement of the needle as the needle is withdrawn into the syringe.

It is an object of the present invention to provide a new and improved hypodermic syringe.

A further object of the present invention is to provide a disposable needle assembly for mounting to a hypodermic syringe which allows the needle to be withdrawn into the carpule subsequent to use.

A further object of the present invention is to provide a hypodermic syringe which eliminates needle contact subsequent to use.

Related objects and advantages of the present invention will be apparent from the following description.

BRIEF DESCRIPTION OF THE DRAWINGS

FIG. 1 is a side view of the hypodermic syringe incorporating my new invention.

FIG. 2 is the same view as FIG. 1 only without the needle assembly and carpule mounted to the syringe.

FIG. 3 is an enlarged cross-sectional view of the needle assembly mountable to the syringe of FIG. 2 and showing one design of the needle.

FIG. 4 is a fragmentary view of the needle assembly shown in FIG. 3 only showing an alternate design of the needle.

FIG. 5 is a fragmentary view of the needle assembly shown in FIG. 3 only showing a further alternate design of the needle.

FIG. 6 is the same view as FIG. 1 only showing a fragment thereof and illustrating the withdrawal of the needle into the carpule.

DESCRIPTION OF THE PREFERRED EMBODIMENT

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now more particularly to FIG. 1, there is shown the preferred embodiment of the hypodermic syringe 10 incorporating my new invention. The syringe includes a main frame or carpule housing 11 with a plunger 12 slidably mounted thereto and engageable with the glass anesthetic carpule 13 removably inserted into housing 11. A needle assembly 14 is removably mounted to the end of housing 11 opposite plunger 12.

Carpule housing 11 includes a cylindrical cavity 15 for receiving the glass anesthetic carpule 13. Plunger 12 has a rod-shaped main body 16 with an outer end 17 configured as a handle or finger hold and an inner pointed end 17 located within cavity 15. End 18 of housing 11 includes a cylindrical passage 19 allowing the plunger to slidably move relative to the housing and position the pointed end 17 at various positions along the length of cavity 15. The opposite end 19 of housing 11 has a threaded boss 20 mounted thereto with a needle passage 21 extending through boss 20 and into cavity 15.

The needle assembly 14 (FIG. 3) has an internally threaded hub shaped main body 22 with the internal threads 23 meshingly engagable with the external threads of boss 20. Hypodermic needle 24 is slidably mounted to passage 25 enabling the inner end 26 of needle 24 to extend through passage 21 and into cavity 15. The outer end 29 has a conventional pointed configuration. Sealing means 27 such as an O-ring is mounted to hub 22 and extends around needle 24 to prevent fluid flow between the outer cylindrical surface of the needle and hub 22. The O-ring 27 may be positioned at the outer distal end 28 of the hub within passage 25.

Glass anesthetic carpule 13 (FIG. 1) includes a cylindrical, hollow main body 30 having a plug 31 sealingly mounted to one end thereof and produced from a material sufficiently soft to allow end 26 of needle 24 to extend piercingly therethrough so as to be in liquid communication with the interior of the carpule. In one embodiment, plug 31 is produced from rubber which sealingly engages needle 24 preventing fluid flow between the exterior surface of the needle and the plug. Plug 31 is fixedly secured to the cylindrical main body 30 allowing the needle to pierce the plug and extend into the carpule without relative motion occurring between plug 31 and cylindrical main body 30. The opposite end of cylindrical main body 30 includes a similar plug 32 which is sealingly mounted thereto, but which is slidable with respect to the interior surface of main body 30. Thus, once end 17 of plunger 12 extends into plug 32, further inward travel of the plunger causes plug 32 to move toward plug 31 forcing the injectable material within the carpule outwardly through the needle. Plug 32 is sufficiently wide to allow end 26 of the needle to extend therein once plug 32 is forced against end 26 at the most inward position of the plunger.

Prior to use of hypodermic syringe 10, carpule 13 is inserted into cavity 15 with plug 31 located adjacent end 19 and slidable plug 32 adjacent pointed plunger end 17. Thus, it is necessary when installing the carpule to force pointed end 17 into plug 32. Plunger end 17 is shaped to enable the pointed end to be inserted into the plug, but which will resist disengagement of end 17 from plug 32 when the plunger is withdrawn. Thus, in the embodiment depicted in FIG. 2, a plurality of stop surfaces 40 are located on the aft side of pointed end 17 to limit disengagement of the plunger from slidable plug 32. Next, needle assembly 14 is threadedly mounted to boss 20 thereby forcing inner end 26 of the needle through stationary plug 31 of carpule 13. Projection 41 is fixedly secured to needle 24 and is normally positioned adjacent the internal frusto conical surface 42 of main body 22. Thus, movement of the needle in the direction of arrow 43 is prevented due to the contact between projection 41 and surface 42. The needle is then extended into the patient and plunger 17 is depressed thereby injecting the material within the carpule into the patient. Once the needle is withdrawn from the patient, the plunger is further depressed until end 26 of the needle is forced into slidable plug 32. Once the needle end has pierced plug 32, the plunger is withdrawn in the direction of arrow 44 pulling the needle through needle housing 22, boss 20 and completely into carpule 13. As depicted in FIG. 6, plunger 12 is being withdrawn in the direction of arrow 44 casuing travel of plug 32 in the same direction and pulling the needle completely into the carpule isolating the pointed needle end 29. The carpule may then be removed from cavity 15 while being disengaged from the plunger readying the syringe for receipt of the next carpule and needle assembly.

Various designs of end 26 may be provided to enable the needle to pierce and be secured to slidable plug 32. In the design shown in FIG. 3, a plurality of barbs 45 are formed on needle end 26 and extend cantileveredly outward from the needle and in the direction of arrow 43. In FIG. 4, the inner end of the needle includes a spiral shaped screw thread 46 formed thereon, whereas in FIG. 5, the inner needle end includes a plurality of circular and independent threads 47 formed thereon. A variety of other types of friction means may be provided on end 25 such as barbs 45 and threads 46 and 47 to prevent relative motion between the needle and plug 32 once the needle and plug are engaged. Passage 21 of boss 20 must be sufficiently large in diameter to enable barbs 45, threads 46 and 47, as well as projection 41 to pass therethrough as the needle is pulled into the carpule.

Many variations are contemplated and included in the present invention. For example, the drawings depict a retractable hypodermic needle utilized in association with a syringe for receiving a removable carpule. While not shown in the drawings, it is to be understood that the present invention also includes a retractable hypodermic needle which is utilized with a disposable syringe having the injectable material provided within the syringe at the time of manufacture. Therefore, in such a case, the syringe would not have a removable carpule. Instead, the syringe includes a housing having the injectable material therein and into which the hypodermic needle is retracted after use.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A hypodermic syringe comprising:
   a carpule housing,
   a carpule positioned in said housing for holding material to be injected;
   a hollow needle with a pointed outer end and an inner end extending into said carpule;
   a plunger slidable mounted to said housing and having a first end located outwardly of said housing for engagement by the user to move the plunger relative to said housing and a second end extending into said carpule and lockable with said inner end when said plunger is moved through said carpule;
   mounting means engaged with said needle and said housing operable to hold said needle but yieldable to allow said plunger to pull said needle completely into said carpule as said plunger is pulled outwardly protecting the user from said pointed outer end upon completion of use; and wherein:
   said mounting means is operable to limit relative motion between said needle and said housing as said plunger is pushed into said housing;
   said inner end of said needle includes friction means thereon lockable with said second end of said plunger when said second end is forced adjacent said inner end; and,
   said carpule includes a plate shaped configuration of yieldable material into which said second end of said plunger extends and into which said inner end of said needle is inserted as said plunger is forced to the most inward position locking said plunger to said needle and withdrawing same into said carpule as said plunger is pulled outwardly.

2. A hypodermic syringe comprising:
   a carpule housing;
   a carpule positioned in said housing for holding material to be injected;
   a hollow needle with a pointed outer end and an inner end extending into said carpule;
   a plunger slidable mounted to said housing and having a first end located outwardly of said housing for engagement by the user to move the plunger relative to said housing and a second end extending into said carpule and lockable with said inner end when said plunger is moved through said carpule;
   mounting means engaged with said needle and said housing operable to hold said needle but yieldable to allow said plunger to pull said needle completely into said carpule as said plunger is pulled outwardly protecting the user from said pointed outer end upon completion of use; and wherein:
   said mounting means includes a main body mounted on said housing and a passage in said main body through which said needle extends and is slidable, said needle and said main body include cooperating stop means limiting outward movement of said needle when said plunger is pushed into said carpule but not limiting inward movement of said needle as said needle is withdrawn into said carpule by said plunger.

3. The hypodermic syringe of claim 9 wherein: said inner end of said needle includes friction means thereon lockable with said second end of said plunger when said second end is forced adjacent said inner end.

4. The hypodermic syringe of claim 3 wherein: said friction means includes a projection formed on said inner end.

5. The hypodermic syring of claim 3 wherein: said friction means includes a plurality of barbs formed on said inner end.

6. The hypodermic syringe of claim 3 wherein: said friction means includes a screw thread formed on said inner end.

7. The hypodermic syringe of claim 3 wherein: said friction means includes a plurality of circular threads formed on said inner end.

8. The hypodermic syringe of claim 2 wherein: said main body includes an internally threaded cavity in mounting engagement with said housing and sealing means surrounding said passage limiting fluid flow between said needle and said main body; said stop means includes a projection on said needle interferingly engagable with said main body limiting outward movement of said needle; said inner end of said needle is spaced from said mounting means a distance to extend into said carpule as said main body is threaded onto said housing.

9. A needle assembly for mounting to a hypodermic syringe comprising:
a hollow needle with a pointed outer end and an inner end; and,
mounting means including a main body removably mountable on said syringe and further including a passage in said main body through which said needle extends and is slidable, said needle and said main body including cooperating stop means limiting outward movement in a direction from said inner end to said outer end of said needle relative to said main body but not limiting inward movement in a direction reverse to said outward movement of said needle as said needle is withdrawn into said syringe.

10. The needle assembly of claim 9 wherein:
said main body includes an internally threaded cavity mountingly engagable with said housing and further includes sealing means surrounding said passage limiting fluid flow between said needle and said main body, said stop means includes a projection on said needle interferingly engagable with said main body limiting outward movement of said needle.

11. The needle assembly of claim 10 wherein: said inner end of said hollow needle includes friction means thereon lockable with said syringe.

12. The needle assembly of claim 11 wherein: said friction means includes a projection formed on said inner end.

13. The hypodermic syringe of claim 12 wherein: said friction means includes a plurality of barbs formed on said inner end.

14. The hypodermic syringe of claim 12 wherein: said friction means includes a screw thread formed on said inner end.

15. The hypodermic syringe of claim 12 wherein: said friction means includes a plurality of circular threads formed on said inner end.

16. A hypodermic syringe comprising:
a housing for holding material to be injected;
a hollow needle with a pointer outer end and an inner end extending into said housing;
a plunger slidable mounted to said housing and having a first end located outwardly of said housing for engagement by the user to move the plunger relative to said housing and a second extending into said housing and lockable with said inner end; and,
mounting means mounting said needle to said housing and including means operable to limit outward movement of said needle in a direction from said inner end to said outer but operable to allow said plunger to pull said needle completely into said housing as said plunger is pulled outwardly projecting the user from said outer pointed end upon completion of use.

17. A hypodermic syringe comprising:
a carpule housing;
a carpule removably positionable in said housing and holding material to be injected;
a hollow needle with a pointed outer end and an inner end extendable into said carpule when said carpule is inserted into said housing;
a plunger slidable mounted to said housing and having a first end located outwardly of said housing for engagement by the user to move the plunger relative to said housing and a second end extending into said carpule when said said carpule is inserted into said housing and lockable with said inner end when said plunger is moved through said carpule; and,
mounting means mounting said needle to said housing and including means operable to limit outward movement of said needle in a direction from said inner end to said outer end but operable to allow said plunger to pull said needle completely into said housing as said plunger is pulled outwardly projecting the user from said outer pointed end upon completion of use.

18. The hypodermic syringe of claim 17 wherein: said mounting means is operable to disengage from said needle when said plunger pulls said needle into said carpule allowing said carpule with needle to be removed from said housing and discarded.

19. A needle assembly for mounting to a hypodermic syringe comprising:
a hollow needle with a pointed outer end and an inner end; and,
mounting means including a main body mountable on said syringe and further including a passage in said main body through which said needle extends and is slidable, said needle and said main body including cooperating stop means limiting outward movement in a direction from said inner end to said outer end of said needle relative to said main body but not limiting inward movement in a direction reverse to said outward movement of said needle as said needle is withdrawn into said syringe.

* * * * *